US012708734B2

(12) United States Patent
Schnaars et al.

(10) Patent No.: US 12,708,734 B2
(45) Date of Patent: Aug. 18, 2026

(54) ABSORPTION ARRANGEMENT WITH A CO2 ABSORBER AND A WATER TRAP AND PROCESS FOR FILTERING OUT CO2

(71) Applicant: Drägerwerk AG & Co. KGaA, Lübeck (DE)

(72) Inventors: Henryk Schnaars, Lübeck (DE); Marcel Prieske, Lübeck (DE)

(73) Assignee: Drägerwerk AG & Co. KGaA, Lübeck (DE)

(*) Notice: Subject to any disclaimer, the term of this patent is extended or adjusted under 35 U.S.C. 154(b) by 818 days.

(21) Appl. No.: 18/149,723

(22) Filed: Jan. 4, 2023

(65) Prior Publication Data

US 2023/0226307 A1 Jul. 20, 2023

(30) Foreign Application Priority Data

Jan. 7, 2022 (DE) ..................... 10 2022 100 286.1

(51) Int. Cl.

| | |
|---|---|
| ***A61M 16/22*** | (2006.01) |
| ***A61M 16/00*** | (2006.01) |
| ***A61M 16/08*** | (2006.01) |
| ***B01D 53/04*** | (2006.01) |

(52) U.S. Cl.

CPC ........ *A61M 16/22* (2013.01); *A61M 16/0808* (2013.01); *B01D 53/0407* (2013.01); *A61M 16/0066* (2013.01); *A61M 16/0891* (2014.02); *B01D 2257/504* (2013.01); *B01D 2259/4533* (2013.01)

(58) Field of Classification Search

CPC .......... A61M 16/0057; A61M 16/0066; A61M 16/0808; A61M 16/0891; A61M 16/1065; A61M 16/22; B01D 2257/504; B01D 2259/4533; B01D 53/002; B01D 53/0407

See application file for complete search history.

(56) References Cited

U.S. PATENT DOCUMENTS 4,210,137 A * 7/1980 Henkin ................ A61M 16/22 128/200.24
4,502,876 A 3/1985 Behnke, Jr. et al.

(Continued)

FOREIGN PATENT DOCUMENTS

CN 203816013 U 9/2014
CN 106999695 A 8/2017

(Continued)

*Primary Examiner* — Joseph D. Boecker

(74) *Attorney, Agent, or Firm* — McGlew and Tuttle, P.C.

(57) ABSTRACT

An absorption arrangement (100) includes a CO2 absorber (1) and a water trap (2). Such an absorption arrangement (100) is used with a process for filtering carbon dioxide from a gas mixture by absorption. The gas mixture flows from a source through the absorption arrangement (100) to a sink in the following way: through a supply fluid guide unit (3), through a lower deflecting fluid guide unit (9), through CO2 absorption material (4), through an upper deflecting fluid guide unit (6), through an intermediate connecting conduit (33), through the water trap (2) and through a discharge fluid guide unit (34). The gas mixture flows vertically or obliquely upward through the CO2 absorber (1) and vertically or obliquely downward through the intermediate connecting conduit (33) to the water trap (2).

20 Claims, 7 Drawing Sheets

(56) References Cited

U.S. PATENT DOCUMENTS

| | | | | |
|---|---|---|---|---|
| 6,619,289 | B1 * | 9/2003 | Mashak | A61M 16/22 128/205.12 |
| 7,850,765 | B2 | 12/2010 | Kleinschmidt | |
| 2007/0051367 | A1 * | 3/2007 | Mashak | A61M 16/1045 128/203.12 |
| 2009/0107505 | A1 * | 4/2009 | Kleinschmidt | A61M 16/22 128/205.28 |
| 2010/0199993 | A1 | 8/2010 | Koulechov et al. | |
| 2011/0150733 | A1 | 6/2011 | Dube et al. | |
| 2012/0003722 | A1 | 1/2012 | Polak et al. | |
| 2017/0266407 | A1 * | 9/2017 | Heesch | A61M 16/22 |

FOREIGN PATENT DOCUMENTS

| | | | |
|---|---|---|---|
| CN | 109395227 | A | 3/2019 |
| DE | 19901590 | C1 | 7/2000 |
| DE | 102007046533 | B3 | 7/2008 |
| DE | 102009024040 | A1 | 12/2010 |
| EP | 1230943 | B1 | 6/2004 |
| RU | 174585 | U1 | 10/2017 |

* cited by examiner 100
7.1
7.2
40.2
7
33
33.a
33.b
34.b
40.1
34
34.a
5
5.1
2.1
2

100
7.1
7.2
40.2
7
5
9
5.1

40.1
33.b
33
33.a
2
2.1

7.1
40.1
7.2
3.2
7
5
4
3
4
1
6
5
40.2
6.2
7.2
7.1
33
33.b
33.a
3.1
34.1

7.1
40.1
7.2
7
5
4
3
4
1
6
5
40.2
6.2
7.2
7.1
33
33.b
33.a
3.1
34.1

ABSORPTION ARRANGEMENT WITH A $CO2$ ABSORBER AND A WATER TRAP AND PROCESS FOR FILTERING OUT $CO2$

CROSS REFERENCE TO RELATED APPLICATIONS

This application claims the benefit of priority under 35 U.S.C. § 119 of German Application 10 2022 100 286.1, filed Jan. 7, 2022, the entire contents of which are incorporated herein by reference.

TECHNICAL FIELD

The invention relates to an absorption arrangement comprising a CO2 absorber and a water trap, and to a process for filtering by absorption carbon dioxide from a gas mixture using such an absorption arrangement.

BACKGROUND

The task of filtering out carbon dioxide from a gas mixture occurs, for example, during artificial respiration of a patient. The patient is supplied with a gas mixture, this gas mixture comprising oxygen and optionally an anesthetic. The gas mixture exhaled by the patient is known to comprise carbon dioxide (CO2) and the gas mixture flows back to the ventilator. The carbon dioxide is to be filtered out of this gas mixture before the gas mixture is conveyed back to the patient.

U.S. Pat. No. 4,502,876 discloses an absorption arrangement connectable to a rebreathing apparatus. The gas mixture flows downwardly through a tube 32 into a perforated sleeve 20 and outwardly from the sleeve 20 into a filter 13 comprising a CO2 absorbing material 24. The gas mixture exits through openings in the shell surface of the filter 13 and enters a tubular gap between the filter 13 and a metallic tube 14. The gas mixture flows downwardly in this gap and enters an inner bag (flexible container 15), and from there continues downwardly into an outer bag (flexible container 16). The gas mixture flows upwardly from the outer bag 16 into a space above the filter 13 and further upwardly through a tube 31. The tube 31 surrounds the tube 32, and condensed liquid settles on the tube 14 and drips down into the outer bag 16.

SUMMARY

It is the object of the invention to provide an absorption arrangement with a CO2 absorber and a process which are capable of absorbing carbon dioxide from a gas mixture flowing through the CO2 absorber and have a better effect than known absorption arrangements and processes.

The object is achieved by an absorption arrangement having features according to the invention and by a process having features according to the invention. Advantageous embodiments are indicated herein. Advantageous embodiments of the absorption arrangement according to the invention are, as far as useful, also advantageous embodiments of the process according to the invention and vice versa.

The absorption arrangement according to the invention comprises a supply fluid guide unit and a discharge fluid guide unit. The supply fluid guide unit is at least temporarily connected or connectable to a source of a gas mixture. The discharge fluid guide unit is at least temporarily connected to a sink for a gas mixture or can be connected to such a sink. In one embodiment, the supply fluid guide unit is connectable to a source-side coupling unit, wherein the source-side coupling unit is in fluid communication with the source. The discharge fluid guide unit is connectable to a sink-side coupling unit, wherein the sink-side coupling unit is in fluid communication with the sink.

A "fluid guide unit" is understood to be a component which is capable of guiding a fluid, in particular a gas or a liquid, along a predetermined path (trajectory). This component completely or at least largely prevents the fluid from leaving this path. The fluid guide unit comprises two openings through which a fluid can flow into the fluid guide unit and/or exit from the fluid guide unit. In particular, the fluid guide unit may be configured as a rigid tube or as a flexible hose, or may comprise a tube and/or a hose, including a two-lumen hose. A fluid connection is established between a first and a second units if a fluid can flow from the first unit to the second unit. It is possible that the fluid can flow directly from the first unit to the second unit. It is also possible that the two units are spaced apart from each other and that a fluid guide unit establishes the fluid connection.

The absorption arrangement according to the invention further comprises a CO2 absorber and a water trap. The CO2 absorber is capable of absorbing carbon dioxide (CO2) and thereby filtering carbon dioxide from a gas mixture flowing through the CO2 absorber. In other words: The content of carbon dioxide in a gas mixture flowing through the CO2 absorber is less after exiting the CO2 absorber than when entering the CO2 absorber. Ideally, the exiting gas mixture no longer contains any carbon dioxide at all. The water trap is able to absorb moisture, especially water. The water trap comprises a corresponding container or receptacle.

Furthermore, the absorption arrangement according to the invention comprises a connecting fluid guide unit. The connecting fluid guide unit connects the CO2 absorber to the water trap.

In addition, the absorption arrangement according to the invention comprises a lower deflecting fluid guide unit and an upper deflecting fluid guide unit. Each deflecting fluid guide unit is capable of changing the direction of a gas mixture flowing through the deflecting fluid guide unit, preferably by an angle of at least 90 degrees, more preferably of at least 150 degrees. The terms "top" and "bottom" refer to an orientation in an operative state (use state) of the absorption arrangement. In the operative state, the upper deflecting fluid guide unit is located vertically or obliquely above the lower deflecting fluid guide unit.

The absorption arrangement according to the invention is configured such that in an operative state a gas mixture flowing from the source to the sink is forced to pass through the absorption arrangement on the following path:

- first through the supply fluid guide unit,
- then through the lower deflecting fluid guide unit,
- then vertically or obliquely (diagonally) upwards through the CO2 absorption material,
- then through the upper deflecting fluid guide unit,
- then vertically or obliquely (diagonally) downwards through the connecting fluid guide unit,
- then through the water trap, and
- then through the discharge fluid guide unit.

Of course, it is possible that a relatively small amount of the gas mixture will leave this path due to inevitable gaps and other leaks.

The terms "vertically or obliquely downwards" and "vertically or obliquely upwards" denote a flow direction which deviates from the vertical by at most 60 degrees, preferably by at most 45 degrees, particularly preferably by at most 30 degrees. Such a flow direction is obtained in the operative state of the absorption arrangement according to the invention. Outside such an operative state, the absorption arrangement may be positioned differently, and therefore fluid guide units may be oriented differently in space.

The absorption arrangement according to the invention comprises a $CO_2$ absorber and a water trap. In many cases, the invention eliminates the need to provide two different and spatially separated components, namely a $CO_2$ absorber and a water trap separate therefrom. These two separate components would in many cases require more space and/or more and/or longer fluid guiding units. Furthermore, in many cases it would be necessary to monitor two components in two different locations and to replace them if necessary. Thanks to the invention it is possible in many cases to replace and thereby renew a single unit.

According to the invention, the gas mixture is deflected on its path from the source to the sink first by the lower and then by the upper deflecting fluid guide unit. On its way from the lower to the upper deflecting fluid guide unit, the gas mixture flows through the $CO_2$ absorption material. In many cases, the configuration of the absorption arrangement causes the gas mixture to flow through the entire $CO_2$ absorption material and not leave the $CO_2$ absorption material at a point between the lower and upper deflecting fluid guide units. This ensures that the absorption material in the $CO_2$ absorber is fully utilized before the $CO_2$ absorber needs to be replaced. Even if one region inside the $CO_2$ absorption material is completely saturated and cannot absorb any more carbon dioxide, another region is still able to absorb carbon dioxide unless the $CO_2$ absorption material is completely depleted and needs to be replaced. In many cases, therefore, this embodiment extends the life of the $CO_2$ absorber compared to other possible embodiments. The $CO_2$ absorber needs to be replaced less frequently.

The absorption arrangement according to the invention causes the gas mixture to flow vertically or obliquely upwards through the $CO_2$ absorption material. The inventors have found in internal experiments that this feature leads to a higher absorption effect than another possible flow direction through the $CO_2$ absorption material due to a different positioning of the $CO_2$ absorption material in space. More specifically, a greater proportion of the carbon dioxide, ideally all of the carbon dioxide, is filtered out of the gas mixture flowing through the $CO_2$ absorption material. With a different flow direction or absorber positioning, a smaller proportion is often filtered out.

This effect is further increased by a preferred embodiment in which in the operative state the lower deflecting fluid guide unit is located vertically or obliquely below the $CO_2$ absorption material, and the $CO_2$ absorption material is located vertically or obliquely below the upper deflecting fluid guide unit. "Below" comprises the options vertically or obliquely below. This effect is further increased by a preferred embodiment of the $CO_2$ absorber. According to this embodiment, the $CO_2$ absorber comprises as the $CO_2$ absorption material an absorbent material, preferably a loose-flowable or bulk absorbent material, which preferably comprises activated carbon or soda lime, and an own housing around the $CO_2$ absorbent material.

According to the invention, the gas mixture flows vertically or obliquely downwards from the $CO_2$ absorber to the water trap. As a result, liquid droplets that may be contained in the gas mixture or may occur due to condensation also flow downward and remain in the water trap. In many cases, therefore, the invention causes liquid droplets to no longer be present in the gas mixture downstream of the water trap.

Preferably, the gas mixture flows vertically or obliquely downwards through the supply fluid guide unit or at least vertically or obliquely downwards through a section of the supply fluid guide unit. This embodiment increases the reliability that the gas mixture actually flows to the lower deflecting fluid guide unit, and that no undesired backflow or backpressure in the opposite direction occurs. This advantage often occurs because in many cases the gas mixture is heavier than ambient air, for example if it also contains anesthetic.

In many cases, an exothermic chemical reaction takes place in the $CO_2$ absorber while a gas mixture is flowing through the $CO_2$ absorber. This chemical reaction causes the $CO_2$ absorber to bind carbon dioxide in the gas mixture. Heat is released during the chemical reaction. As a rule, this heats up the gas mixture as it flows through the $CO_2$ absorber.

Various embodiments are possible to re-cool the gas mixture. Some preferred embodiments are described below to achieve this effect.

The gas mixture flows from the $CO_2$ absorption material through the upper deflecting fluid guide unit and the connecting fluid guide unit to the water trap. In particular, when the chemical reaction in the $CO_2$ absorber releases heat, the gas mixture downstream of the $CO_2$ absorber is generally warmer than the ambient air. In a preferred embodiment, the connecting fluid guide unit—or at least a portion of the connecting fluid guide unit—is directly adjacent to an environment surrounding the absorption arrangement. It is also possible that the upper deflecting fluid guide unit—or at least a portion of the upper deflecting fluid guide unit—is directly adjacent to the environment.

The feature that a fluid guide unit is directly adjacent to the environment is to be understood that only the wall of this fluid guide unit separates the gas mixture flowing through from the environment, but not a further wall which is spaced apart from the wall of the fluid guide unit. A suitable configuration of this wall makes it possible that the wall separates the gas mixture flowing through from the environment in a fluid-tight manner, but establishes a large-area and thus good thermal contact between the gas mixture flowing through the fluid guide unit and the environment. If the gas mixture is warmer than the environment, the gas mixture delivers heat to the environment through the wall and thus cools down.

According to the invention, the gas mixture flows through the supply fluid guide unit and later through the $CO_2$ absorber. In one embodiment, the $CO_2$ absorber surrounds the supply fluid guide unit—or at least a section of the supply fluid guide unit—in the manner of a casing. In one embodiment, the wall of the supply fluid guide unit also forms an inner wall for a chamber accommodating absorption material, this chamber being part of the $CO_2$ absorber.

The feature that the $CO_2$ absorption material surrounds the supply fluid guide unit has in many cases the effect that a large-area and therefore good thermal contact is established between the $CO_2$ absorption material and the supply fluid guide unit. This allows the $CO_2$ absorption material to transfer heat to gas mixtures in the supply fluid guide unit. The gas mixture flows through the supply fluid guide unit and then through the lower deflecting fluid guide unit before entering the $CO_2$ absorption material. An embodiment is made possible in which the lower deflecting fluid guide unit emits heat to the environment.

According to the invention, the gas mixture flows from the $CO_2$ absorption material through the upper deflecting fluid guide unit and the connecting fluid guide unit to the water trap. In one embodiment, the connecting fluid guide unit—or at least a portion of the connecting fluid guide unit—surrounds the CO2 absorption material in the manner of a casing. In one embodiment, the wall of the connecting fluid guide unit also forms an outer wall for a chamber accommodating absorption material, this chamber belonging to the CO2 absorber.

The feature that the connecting fluid guide unit surrounds the CO2 absorption material has in many cases the effect that a large-area and thus good thermal contact is established between the CO2 absorption material and the connecting fluid guide unit. This allows the CO2 absorption material to transfer heat to the connecting fluid guide unit. Preferably, this embodiment is combined with the embodiment that the connecting fluid guide unit is directly adjacent to the environment. As a result, the connecting fluid guide unit can absorb heat from the CO2 absorption material and deliver it to the environment.

Thanks to the absorption arrangement according to the invention, the gas mixture has a lower content of carbon dioxide when it leaves the absorption arrangement compared to when it enters the absorption arrangement, ideally no carbon dioxide at all. However, thanks to the thermal contact with the environment and thanks to the water trap, in many cases the temperature and the moisture content at the exit from the absorption arrangement are not significantly higher than or even equal to or lower than at the entry.

In many cases, the moisture content of the gas mixture increases as the gas mixture flows through the CO2 absorber, in particular because water is released during the exothermic chemical reaction in the CO2 absorber and/or because this reaction leads to an increased temperature. Preferably, the gas mixture flows vertically or obliquely upwards through the discharge fluid guide unit or at least vertically or obliquely upwards through a section of the discharge fluid guide unit. This embodiment further increases the reliability that the gas mixture will no longer have liquid droplets downstream from the water trap. Gravity will in many cases prevent liquid droplets from leaving the water trap or at least flowing back to the water trap.

At least one of the features,

- that the gas mixture flows vertically or obliquely downwards through the connecting fluid guide unit to the water trap and
- that the gas mixture flows vertically or obliquely upwards away from the water trap through the discharge fluid guide unit, is particularly advantageous if the gas mixture heats up in the CO2 absorber and cools down again in a subsequent fluid guide unit. In many cases, at least a portion of liquid in the gas mixture condenses on a wall of this fluid guide unit. This liquid then flows vertically or obliquely downwards into the water trap and is collected there. This liquid is prevented from leaving the absorption arrangement.

In a preferred embodiment, the absorption arrangement further comprises an intermediate piece. This intermediate piece is connected to both the source and the sink, or is at least temporarily connectable to both the source and the sink. The CO2 absorber and the water trap are arranged outside the intermediate piece and are directly or indirectly mechanically connected to the intermediate piece. Preferably, the intermediate piece is configured as a rigid component, in particular with at least one fluid guide unit inside.

In an implementation of the embodiment with the intermediate piece, the mechanical connection between the intermediate piece and the CO2 absorber and/or the mechanical connection between the intermediate piece and the water trap can be released again. This form of implementation makes it easier to replace the CO2 absorber and/or the water trap.

The configuration with the intermediate piece avoids the necessity to connect the CO2 absorber or the water trap or a loose fluid guide unit directly to the source or to the sink. The intermediate piece can be configured as an adapter so that several CO2 absorbers of the same type and/or several water traps of the same type can be connected to sources and/or sinks which are configured mechanically differently.

In one embodiment, the absorption arrangement comprises an intermediate piece and a further intermediate piece. The CO2 absorber and the water trap can selectively be mechanically connected to the intermediate piece or to the further intermediate piece. The two intermediate pieces may have different coupling units for connection to a source and/or to a sink. The two intermediate pieces thus function as different adapters.

The embodiment with the intermediate piece and the optional further intermediate piece makes it possible in many cases to continue to use an already existing CO2 absorber (more precisely: an already existing type of a CO2 absorber) and/or an already existing water trap (more precisely: a type of a water trap). The CO2 absorber and/or the water trap can be connected to the intermediate piece. It is not necessary to modify an already existing coupling element with the source or an already existing coupling element with the sink. This embodiment makes it easier to integrate the absorption arrangement according to the invention into an existing system.

According to the embodiment with the intermediate piece, the water trap is mechanically connected to the intermediate piece. In one embodiment, the connecting fluid guide unit is located entirely within the intermediate piece. In another embodiment, the connecting fluid guide unit—or at least a portion of the connecting fluid guide unit—is located outside the intermediate piece and is mechanically connected or connectable to the intermediate piece, in one embodiment releasably connected or connectable. The water trap is in turn mechanically connected to the connecting fluid guide unit. It is possible that a portion of the connecting fluid guide unit is located in the intermediate piece and another portion is located outside the intermediate piece.

In many cases, the embodiment that the connecting fluid guide unit or at least a portion is located outside the intermediate piece results in the connecting fluid guide unit being surrounded by an environment of the absorption arrangement and thereby being able to transfer heat to the environment. Furthermore, this embodiment makes it easier in many cases to empty the water trap and/or to replace it with a new water trap.

In one embodiment, the connecting fluid guide unit is located outside the intermediate piece and is flexible. In one embodiment, the discharge fluid guide unit is also located outside the intermediate piece and is flexible. These two implementations reduce the risk of damaging the water trap or one of the fluid guide units if the absorption arrangement collides with another object.

In one implementation of the first embodiment, the intermediate piece comprises an outer adapter and an inner adapter. The outer adapter is connectable or connected to the source and to the sink. The inner adapter is connected or connectable to the CO2 absorber. The water trap is connected or connectable to the outer adapter or to the inner adapter.

According to the invention, the gas mixture flows through the CO2 absorption material, then through the upper deflecting fluid guide unit and then through the connecting fluid guide unit. In a first implementation of the embodiment with the intermediate piece, the upper deflecting fluid guide unit—or at least a section of the upper deflecting fluid guide unit—is located within the intermediate piece. In this first implementation, the intermediate piece protects to some extent the deflecting fluid guide unit from mechanical damage. In a second implementation, the upper deflecting fluid guide unit—or at least a portion of the upper deflecting fluid guide unit—is located outside the intermediate piece and is mechanically connected to the intermediate piece. In many cases, the second implementation allows the upper deflecting fluid guide unit to transfer heat to the environment.

In one embodiment, the absorption arrangement comprises an outer housing. This outer housing surrounds at least the CO2 absorption material, the water trap and all fluid guide units provided according to the invention. Preferably, the outer housing surrounds the entire absorption arrangement. Preferably, the outer housing is a rigid housing which is impermeable to fluid. Preferably, the outer housing is able to provide a large surface area and thus good thermal contact with the environment so that heat generated during the exothermic chemical reaction is transferred to the environment. In many cases, the embodiment with the outer housing leads to a particularly compact and robust absorption arrangement. In addition, the outer housing protects the other components from mechanical damage to some extent. In many cases, it is relatively easy to grasp and replace the absorption arrangement.

In one implementation of the embodiment with the outer housing, the connecting fluid guide unit—or at least a section of the connecting fluid guide unit—is located between the outer housing and the CO2 absorption material, for example in the manner of a casing. It is possible that the outer housing additionally provides at the same time an outer wall of the connecting fluid guide unit. It is also possible that a wall of the connecting fluid guide unit additionally provides an outer wall of the CO2 absorber. The just described implementation, namely that the connecting fluid guide unit is located between the outer housing and the CO2 absorption material, leads in many cases to the fact that the connecting fluid guide unit can transfer a high amount of heat to the environment.

In one implementation, the outer housing includes an upper housing part and a lower housing part. The two housing parts are mechanically connected to each other, in one embodiment fixedly and in one embodiment detachably (releasably). The upper housing part surrounds at least the CO2 absorption material, the two deflecting fluid guide units, and the connecting fluid guide unit. The lower housing part forms a bottom of the water trap. The terms “top” and “bottom” again refer to an orientation during an operative state (a productive use) of the absorption arrangement.

If the lower housing part is detachably connected to the upper housing part, the water trap can be very easily separated from the upper housing part, emptied, and reconnected, for example with a snap lock or latch or screw lock. When in operative state (productive use), the bottom of the water trap is located below the upper housing part and thus also below the CO2 absorption material and the fluid guide units. As a result, fluid flows vertically or obliquely downwards into the water trap.

The invention can be used in the following application to absorb carbon dioxide from a gas mixture: the gas mixture flows from a patient-side coupling unit through a fluid guide unit to a medical device, in particular to a ventilator. The patient-side coupling unit is positioned or positionable in or on or at the body of a patient. The patient-side coupling unit acts as a source, and the medical device acts as a sink. Thus, the fluid guide unit guides exhaled air from the patient-side coupling unit to the medical device. As is known, exhaled air comprises a higher percentage of carbon dioxide than ambient air. The medical device receives the exhaled air after the exhaled gas mixture has flowed through the absorption arrangement and thereby through the absorption arrangement according to the invention and the absorption arrangement has filtered carbon dioxide from the exhaled air. In one embodiment the medical device is a ventilator. The ventilator is then able to deliver this air back to the patient-side coupling unit. The medical device can also be a stationary or mobile receptacle for exhaled air.

The invention further relates to a ventilation system for artificially respirating a patient. This ventilation system comprises

- a ventilator,
- a patient-side coupling unit,
- an inspiratory fluid connection,
- an expiratory fluid connection, and
- an absorption arrangement according to the invention.

The patient-side coupling unit is positioned or can be positioned in or on the patient’s body. The ventilator is connected to the patient-side coupling unit by the two fluid connections. The two fluid connections are pneumatically isolated from each other such that no fluid can flow from one fluid connection directly into the other fluid connection.

The ventilator is capable of delivering a gas mixture through the inspiratory fluid connection to the patient-side coupling unit.

A gas mixture may flow from the patient-side coupling unit through the expiratory fluid connection to the ventilator during use of the ventilator system. The patient-side coupling unit acts as a source of a gas mixture, in this case as a source of exhaled air. The ventilator acts as a sink for the gas mixture.

In the process of the gas mixture (exhaled air) flowing from the patient-side coupling unit (source) to the ventilator (sink), the gas mixture flows through the absorption arrangement according to the invention. The absorption arrangement filters carbon dioxide out of this gas mixture.

In the following, the invention is described with reference to exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
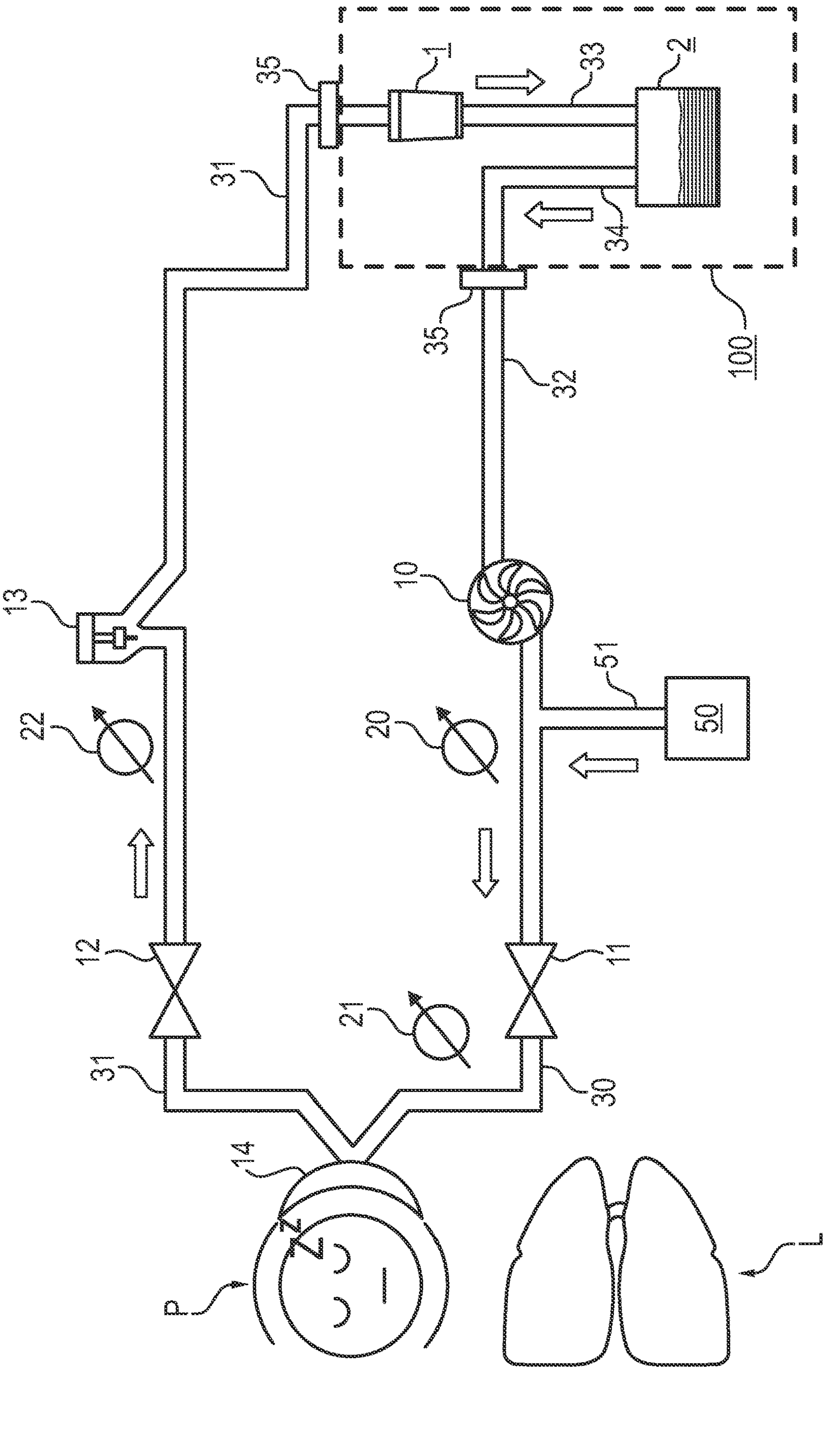
FIG. 1 is a schematic view showing the operative state (use state) of the absorption arrangement according to the invention in a ventilation circuit.

Referring to the drawings, in the exemplary embodiment, the invention is used in a ventilation circuit. In this ventilation circuit, a gas mixture circulates between a ventilator and the lungs L of a patient P. The ventilator maintains the flow of the gas mixture in the ventilation circuit. An inspiratory gas mixture, comprising oxygen and at least one anesthetic, flows from the ventilator through an inspiratory fluid connection to the patient and is inhaled by the patient. An expiratory gas mixture comprising carbon dioxide (CO2) is exhaled by the patient and flows back to the ventilator through an expiratory fluid connection. Because a largely fluid-tight ventilation circuit is established, no anesthetic leaks into the environment.

In order to be able to feed the expiratory gas mixture back to patient P for inhalation, the exhaled carbon dioxide must be removed from the expiratory gas mixture. For this purpose, the expiratory gas mixture is guided through a CO2 absorber. An absorption material in this CO2 absorber, preferably comprising breathing lime (soda lime), binds the carbon dioxide to itself and thereby removes it from the expiratory gas mixture which is guided through the CO2 absorber.

The chemical reaction in the CO2 absorber is exothermic, i.e. the expiratory gas mixture heats up. In addition, the moisture content in the expiratory gas mixture increases. Therefore, moisture in the expiratory gas mixture is caused to condense and collects in a water tank or receptacle belonging to a so-called water trap. The invention relates to an absorption arrangement comprising the CO2 absorber and the water trap.

FIG. 1 shows schematically some of the components of this ventilation circuit. Shown are:

- an absorption arrangement 100 according to the invention, comprising a CO2 absorber 1 and a water trap 2,
- a patient-side coupling unit 14 positioned in or on the body of the patient P, for example a breathing mask or a tube or a catheter,
- a blower 10 of a ventilator, which blower maintains the flow of gas in the ventilation circuit,
- an inspiratory line 30 guiding from the blower 10 to the patient-side coupling unit 14,
- an anesthetic dispenser 50 which produces at least one anesthetic gas mixture comprising an anesthetic,
- an anesthetic feed line 51 guiding from the anesthetic dispenser 50 to the inspiratory line 30 and feeding the anesthetic gas mixture with the anesthetic into the inspiratory line 30,
- an expiratory line having a first section 31 guiding from the patient-side coupling unit 14 to the absorption arrangement 100 and a second section 32 guiding from the absorption arrangement 100 to the blower 10, and
- a line-side coupling unit 35 at the two sections 31 and 32, by which line-side coupling unit the absorption arrangement 100 can be detachably (releasably) connected to both sections 31 and 32 of the expiratory line.

It is also possible that another fluid conveying unit maintains the flow of gas in the ventilation circuit, such as a piston-cylinder unit or a hand-held resuscitator.

The absorption arrangement 100 comprises

- the CO2 absorber 1,
- the water trap 2,
- an intermediate connecting conduit 33 guiding from the CO2 absorber 1 to the water trap 2 and serving as the connecting fluid guide unit, and
- a discharge connecting conduit 34 leading from the water trap 2 to the second section 32.

The expiratory gas mixture flows from the first section 31 to the absorption arrangement 100 and there through the CO2 absorber 1, through the intermediate connecting conduit 33, the water trap 2 and the discharge connecting conduit 34 and then into the second section 32.

The CO2 absorber 1 removes carbon dioxide from the gas mixture flowing through the CO2 absorber 1. The expiratory gas mixture purified of carbon dioxide flows through the intermediate connecting conduit 33 to the water trap 2, where moisture in the expiratory gas mixture condenses and is collected in a container or receptacle of the water trap 2. Moisture is thus taken from the expiratory gas mixture.

A lung pressure valve (positive end expiratory pressure (PEEP) saver valve) 13 in the first section 31 ensures that an end expiratory pressure is maintained in the lungs of the patient P. The PEEP saver valve 13 diverts any excess pressure in the first section 31 to the environment. A pressure sensor 20 measures an indicator for the pressure in the inspiratory line 30, and a pressure sensor 22 measures an indicator for the pressure in the expiratory line 31. A volume flow sensor 21 measures an indicator for the volume flow in the inspiratory line 30. A signal processing control unit (not shown) receives and processes readings from the sensors 20, 21 and 22 and controls depending on the readings an inspiratory valve 11 and an expiratory valve 12. The control unit controls the inspiratory valve 11 with the control gain that the actual time course of the volume flow through or also the actual time course of the pressure in the inspiratory line 30 follows a predetermined time course. Accordingly, the control device controls the expiratory valve 12 with the control gain that the actual time course of the volume flow through or also the actual time course of the pressure in the first section 31 of the expiratory line follows a predetermined time course.

Figure 2B:
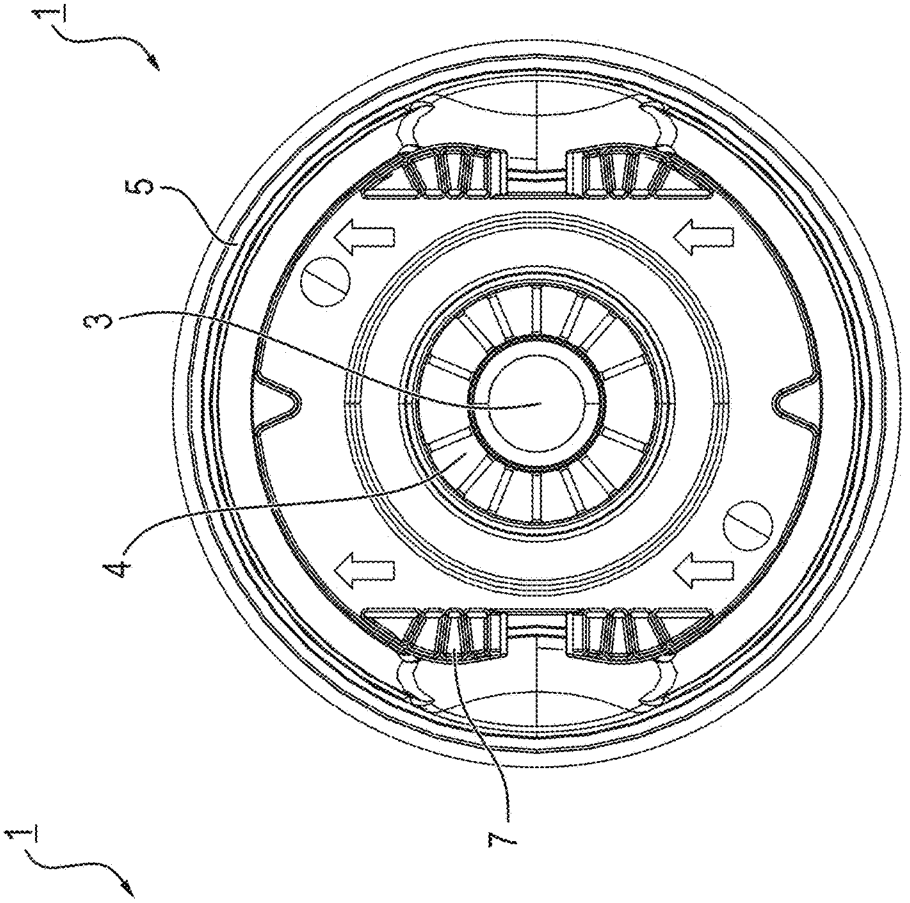
FIG. 2A is a cross-sectional view and FIG. 2B is a top view of a CO2 absorber without water trap.
Figure 2A:
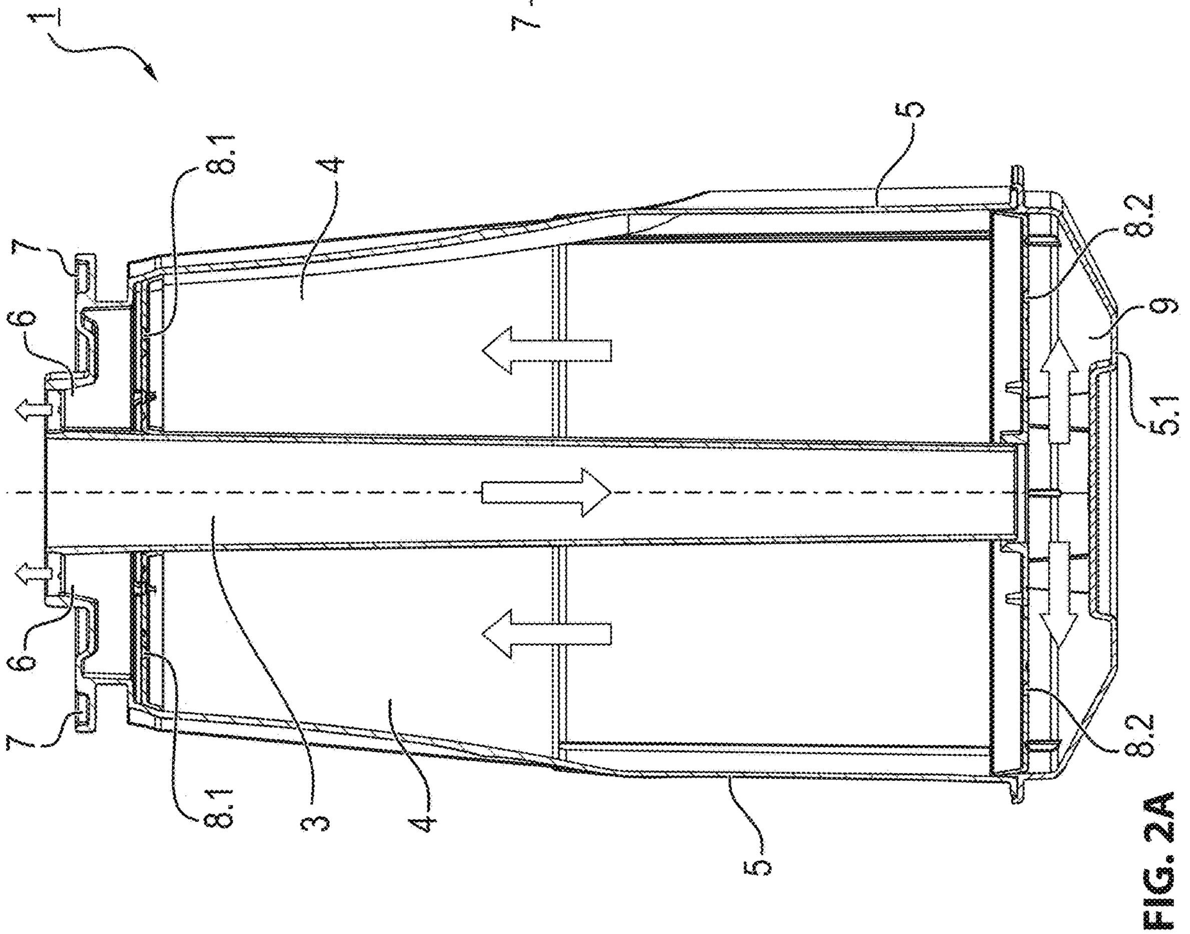

FIG. 2A and FIG. 2B show an exemplary CO2 absorber 1, namely on the left in a sectional view and on the right in a top view. This CO2 absorber 1 can be a component of an embodiment of the absorption arrangement 100 according to the invention. The CO2 absorber 1 according to FIG. 2A and FIG. 2B has the form of a cartridge and comprises

- a preferably rigid housing 5 with a bottom 5.1,
- an absorption material 4 capable of absorbing CO2 and comprising, for example, breathing lime,
- a feed tube 3,
- a discharge cavity 6 above the CO2 absorption material 4,
- an upper sieve 8.1 comprising a dust-protection fleece, the upper sieve 8.1 being arranged between the discharge cavity 6 and the CO2 absorption material 4,
- a lower deflection cavity 9 below the CO2 absorption material 4 and above the bottom 5.1,
- a lower sieve 8.2 between the CO2 absorption material 4 and the deflection cavity 9 and
- an adapter 7 surrounding the discharge cavity 6.

The housing 5 provides a container or receptacle for the CO2 absorption material 4. This container is limited at the bottom by the lower sieve 8.2 and at the top by the upper sieve 8.1. The feed tube 3 is centrally guided through the $CO_2$ absorption material 4. The discharge cavity 6 is in fluid communication with the $CO_2$ absorption material 4, this fluid communication guiding through the upper sieve 8.1.

By means of the adapter 7, the $CO_2$ absorber 1 can be detachably attached to the corresponding line-side coupling unit 35 of the expiratory line 31, 32, for example by means of a snap connection or snap-in connection or screw connection. When the $CO_2$ absorber 1 is connected, the feed tube 3 is in fluid communication with the first section 31 of the expiratory line. The discharge cavity 6 is in fluid communication with the water trap 2 via the intermediate connecting conduit 33, and thus indirectly in fluid communication with the second section 32 of the expiratory line.

If the $CO_2$ absorber 1 is attached to the line-side coupling unit 35, the feed tube 3 is arranged vertically and the housing 5 is located below the adapter 7. The designations "top" and "bottom" refer to an orientation of the $CO_2$ absorber 1 that occurs in an operative state (use state) and attached to the line-side coupling unit 35. The lower sieve 8.2 is permeable to gas, but not to $CO_2$ absorption material 4, and prevents $CO_2$ absorption material 4 from entering the deflection cavity 9. The discharge cavity 6 is located above the absorption material 4. The expiratory gas mixture flows down through the feed tube 3, is deflected at the bottom 5.1 of the housing 5 and flows through the deflection cavity 9 and the lower sieve 8.2 and then up through the absorption material 4. The absorption material 4 removes carbon dioxide from the expiratory gas mixture flowing therethrough. The expiratory gas mixture, purified of carbon dioxide, passes into the discharge cavity 6 and then into the intermediate connecting conduit 33. The arrows in FIG. 2A and FIG. 2B indicate how the gas mixture flows through the $CO_2$ absorber 1. The expiratory gas mixture is forced to flow throughout the $CO_2$ absorber 1 by the configuration of the absorption arrangement 100. As long as the $CO_2$ absorber 1 comprises any $CO_2$ absorption material at all not yet consumed, carbon dioxide will also be absorbed. This might not be the case if the expiratory gas mixture is allowed to escape from the $CO_2$ absorber beforehand.

Note: In internal experiments, the inventors have empirically determined that the $CO_2$ absorption material 4 can absorb more carbon dioxide when the expiratory gas mixture flows through the $CO_2$ absorbent material 4 vertically or obliquely from the bottom up, than when it flows through from the top down or horizontally.

FIG. 3A to FIG. 5B show a first embodiment of the absorption arrangement 100 according to the invention. The absorption arrangement 100 according to the first embodiment comprises

- the $CO_2$ absorber 1 of FIG. 2A and FIG. 2B,
- the water trap 2 with a reservoir for water above a bottom 2.1,
- the intermediate connecting conduit 33,
- the discharge connecting conduit 34,
- a coupling-side intermediate piece 40.1 and
- an absorber-side intermediate piece 40.2.

Figure 3:
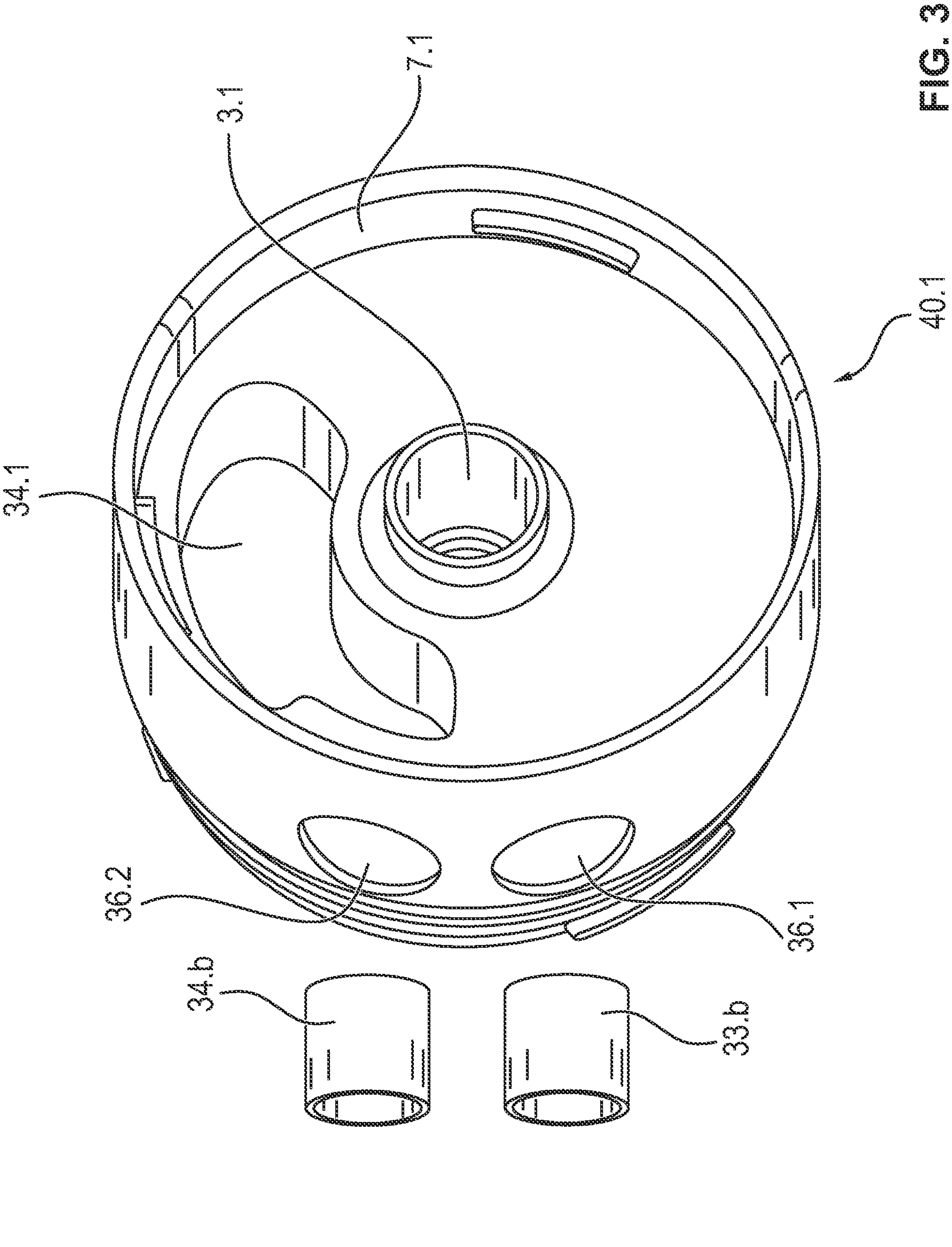
FIG. 3 is a perspective view showing the coupling-side intermediate piece (adapter) of the first embodiment.
Figure 4B:
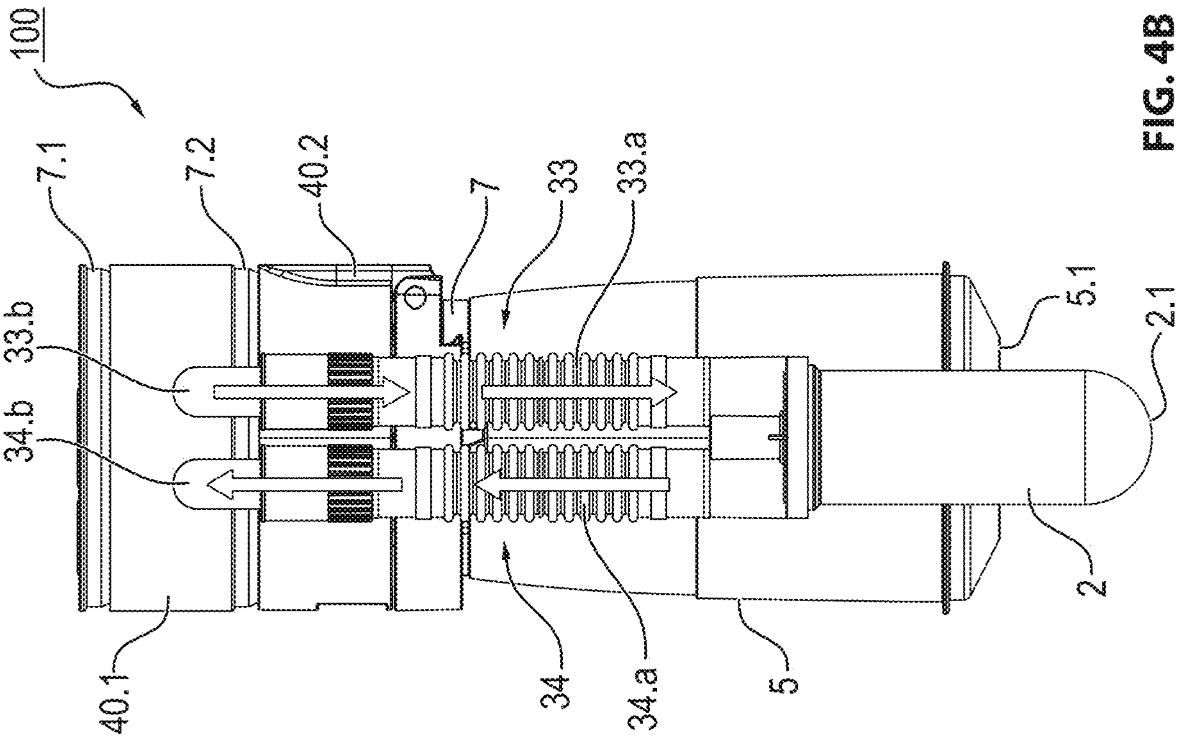
FIG. 4A is a first side view and FIG. 4B is a second side view showing the first embodiment from two different directions.
Figure 4A:
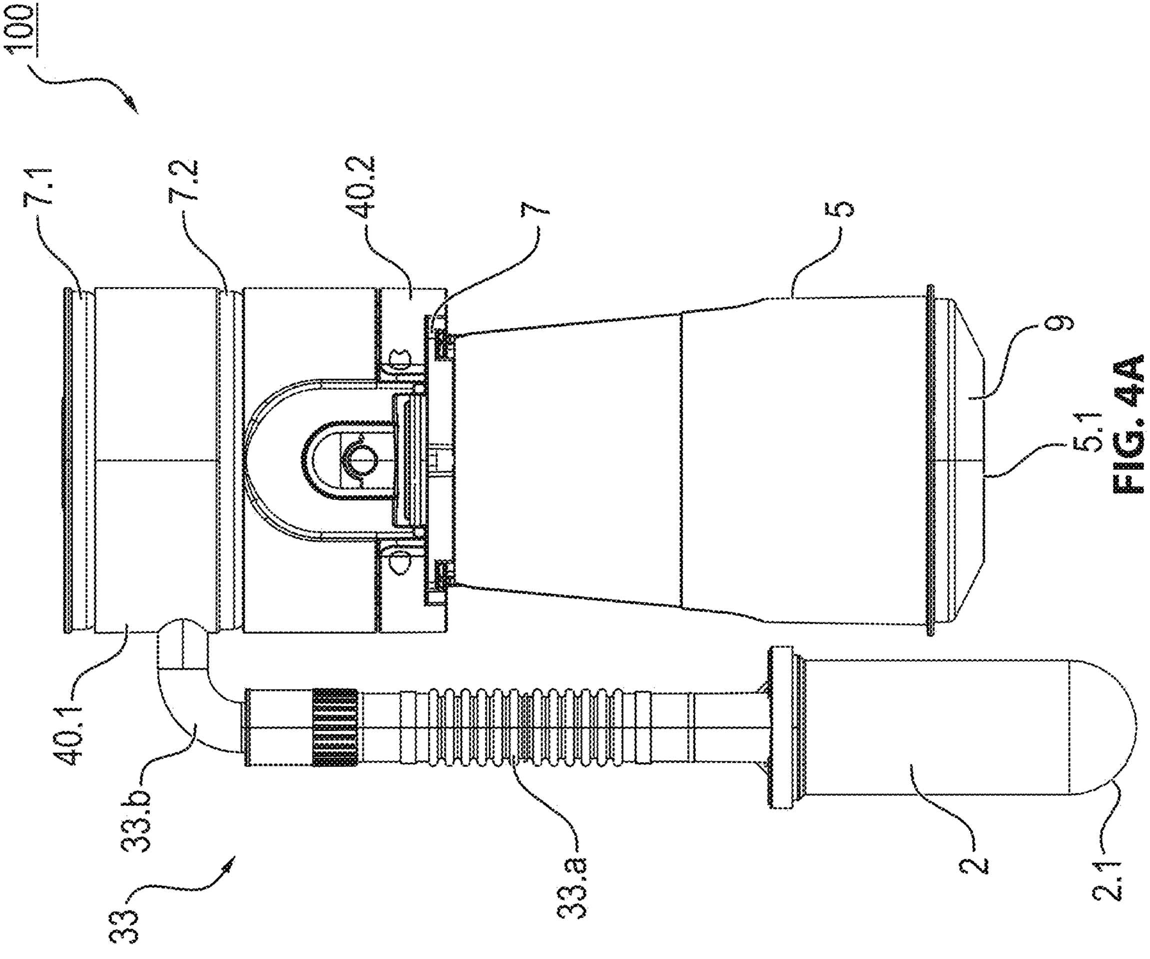
Figure 5B:
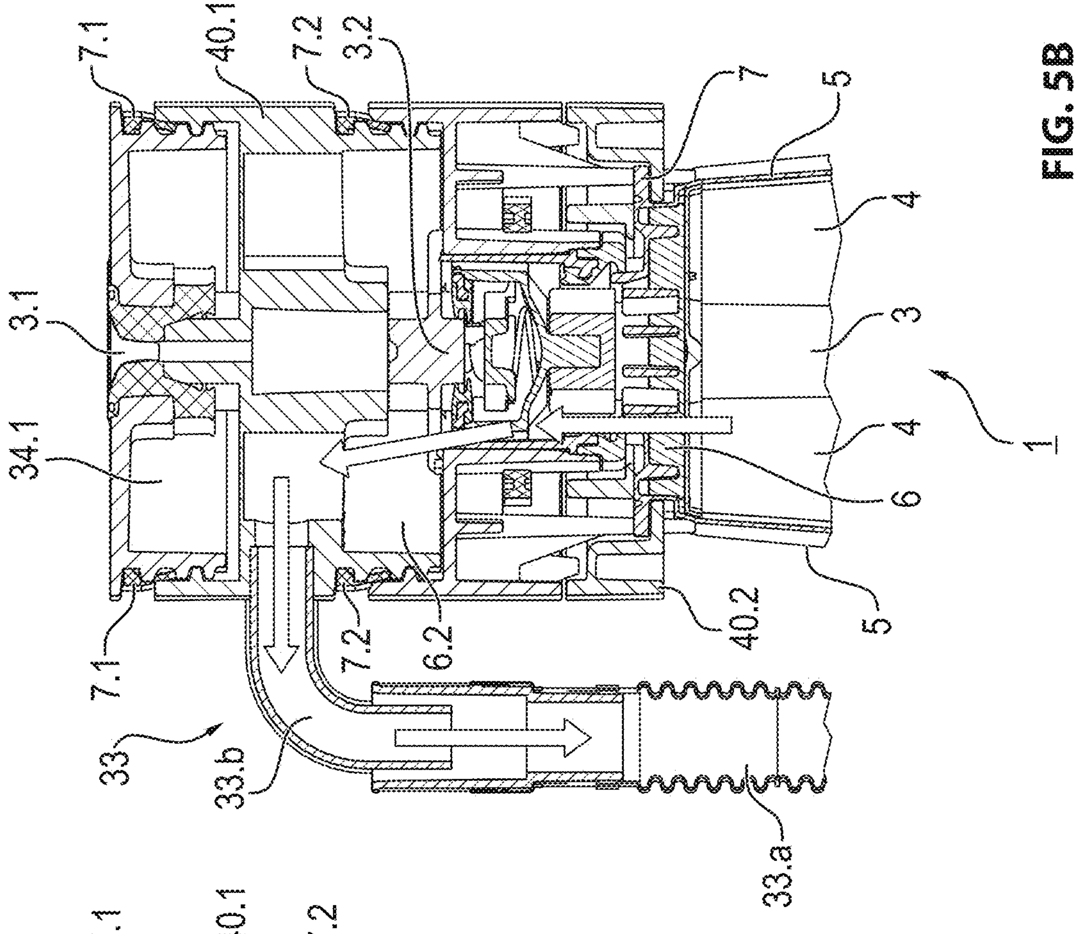
FIG. 5A is a first cross-sectional side view and FIG. 5B is a further cross-sectional side view showing the first embodiment from the same viewing direction.
Figure 5A:
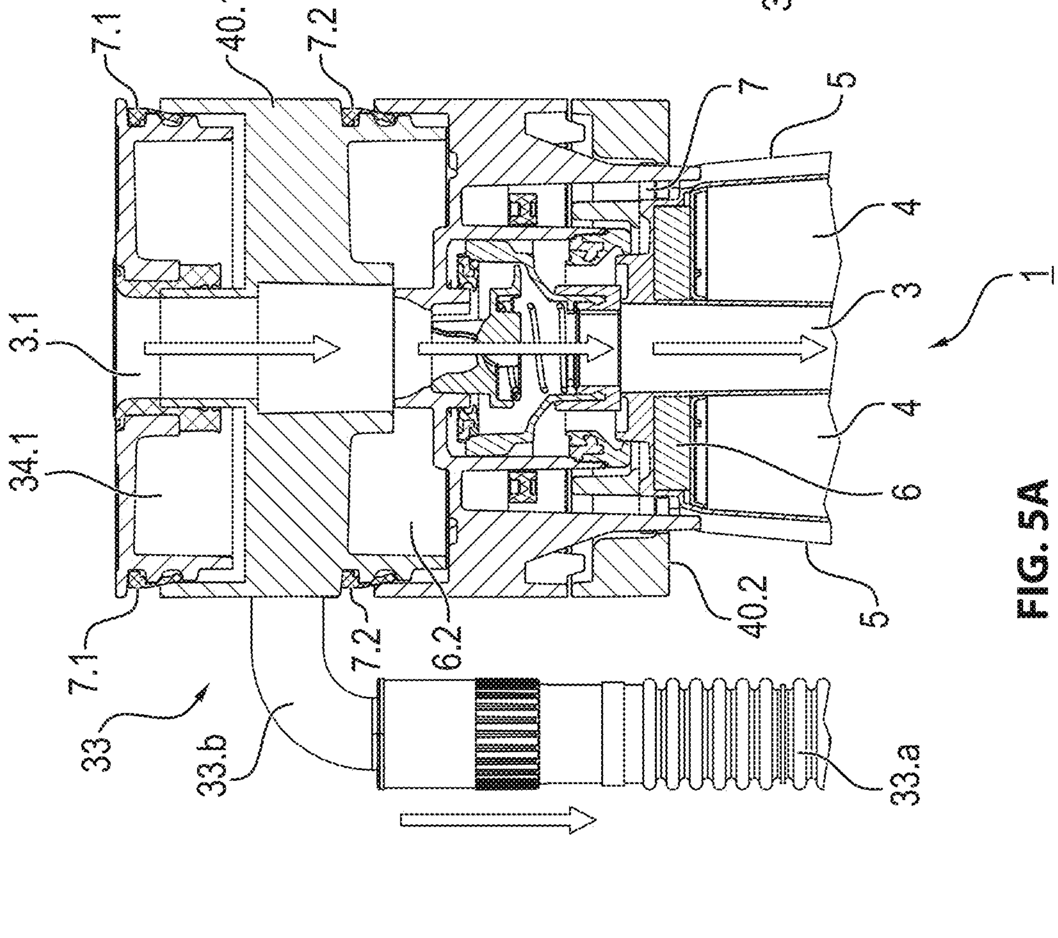

The coupling-side intermediate piece 40.1 of FIG. 3 comprises an adapter 7.1. This adapter 7.1 can be connected, preferably detachably connected, to the line-side coupling unit 35 in the same way as the adapter 7 of the $CO_2$ absorber 1 of FIG. 2. Thanks to an adapter 7.2, the absorber-side intermediate piece 40.2 can be connected, preferably detachably connected, to the coupling-side intermediate piece 40.1. The $CO_2$ absorber 1 is connected, preferably detachably connected, to the absorber-side intermediate piece 40.2.

A coupling-side continuation 3.1 of the feed tube 3 and a coupling-side continuation 34.1 of the discharge connecting conduit 34 are inserted into the coupling-side intermediate piece 40.1. A continuation 3.2 of the feed tube 3 and a continuation 6.2 of the discharge cavity 6 are inserted into the absorber-side intermediate piece 40.2.

The two connecting conduits 33 and 34 each comprise a corrugated hose 33.*a*, 34.*a* and a rigid curved tube 33.*b*, 34.*b*. The two rigid tubes 33.*b*, 34.*b* each comprise a segment in the shape of a quarter circle and two adjacent straight segments and can be inserted into two corresponding receptacles 36.1, 36.2 in the coupling-side intermediate piece 40.1 or are fixedly inserted into these receptacles 36.1, 36.2. Because the two corrugated hoses 33.*a*, 34.*a* are flexible, there is less risk that a connecting conduit 33, 34 or the water trap 2 will break if the absorption arrangement 100 collides with a rigid object. Preferably, the water trap 2 is detachably connected to the two corrugated hoses 33.*a*, 34.*a* so that the water trap 2 can be detached and emptied.

The feed tube 3 and the continuations 3.1, 3.2 function as the supply fluid guide unit in the first embodiment. The intermediate connecting conduit 33 and the corrugated hose 33.*a* act as the connecting fluid guide unit, which connects the $CO_2$ absorber 1 to the water trap 2. The corrugated tube 34.*a*, the rigid tube 34.*b* and the continuation 34.1 belong to the discharge fluid guide unit.

As explained above, heat is released during the process of the absorption material 4 absorbing carbon dioxide. As a result, the expiratory gas mixture is heated as it flows through. The absorption arrangement 100 is capable of releasing heat into the environment at a plurality of locations.

The absorption material 4 surrounds the feed tube 3, and the heated absorption material 4 can therefore release heat to the feed tube 3. The gas mixture heated thereby is deflected in the lower deflection cavity 9, and the bottom of the lower deflection cavity 9 can release heat to the surroundings.

The two connecting conduits 33 and 34 are in thermal contact with the environment. The environment completely surrounds the two connecting conduits 33 and 34. After the gas mixture has flowed through the absorption material 4, it has heated up. Due to the thermal contact with the environment, the gas mixture cools down and water droplets condense on the inner walls of the connecting conduits 33 and 34. These water droplets run downwards into the water trap 2.

The gas mixture flows from the first section 31 through the absorption arrangement 100 according to the first embodiment to the second section 32 in the following way:

- downwards through the continuation 3.1,
- downwards through the continuation 3.2,
- down through the feed tube 3,
- through the deflection cavity 9, where the gas mixture is deflected,
- upwards through the absorption material 4, where carbon dioxide is absorbed,
- upwards through the discharge cavity 6,
- upwards through continuation 6.2, where the gas mixture is deflected in a horizontal direction,
- through the intermediate connecting conduit 33, first along a curve through the tube 33.*b*, so that the gas mixture is deflected downward, and then downward through the corrugated hose 33.*a,*
- through the water trap 2, where condensed water collects,
- through the discharge connecting conduit 34, first upwards through the corrugated tube 34.*a* and then through the tube 34.*b* along a bend, and then
- through continuation 34.1.

This path is indicated by arrows in FIG. 4A, FIG. 4B, FIG. 5A and FIG. 5B. In the first embodiment, the continuation 6.2 and the tube 33.*b* act as the upper deflecting fluid guide unit, and the deflection cavity 9 acts as the lower deflecting fluid guide unit. In one implementation, the deflecting fluid guide units 9, 6.2, 33.*b* deflect the gas mixture about 180 degrees.

Figure 6:
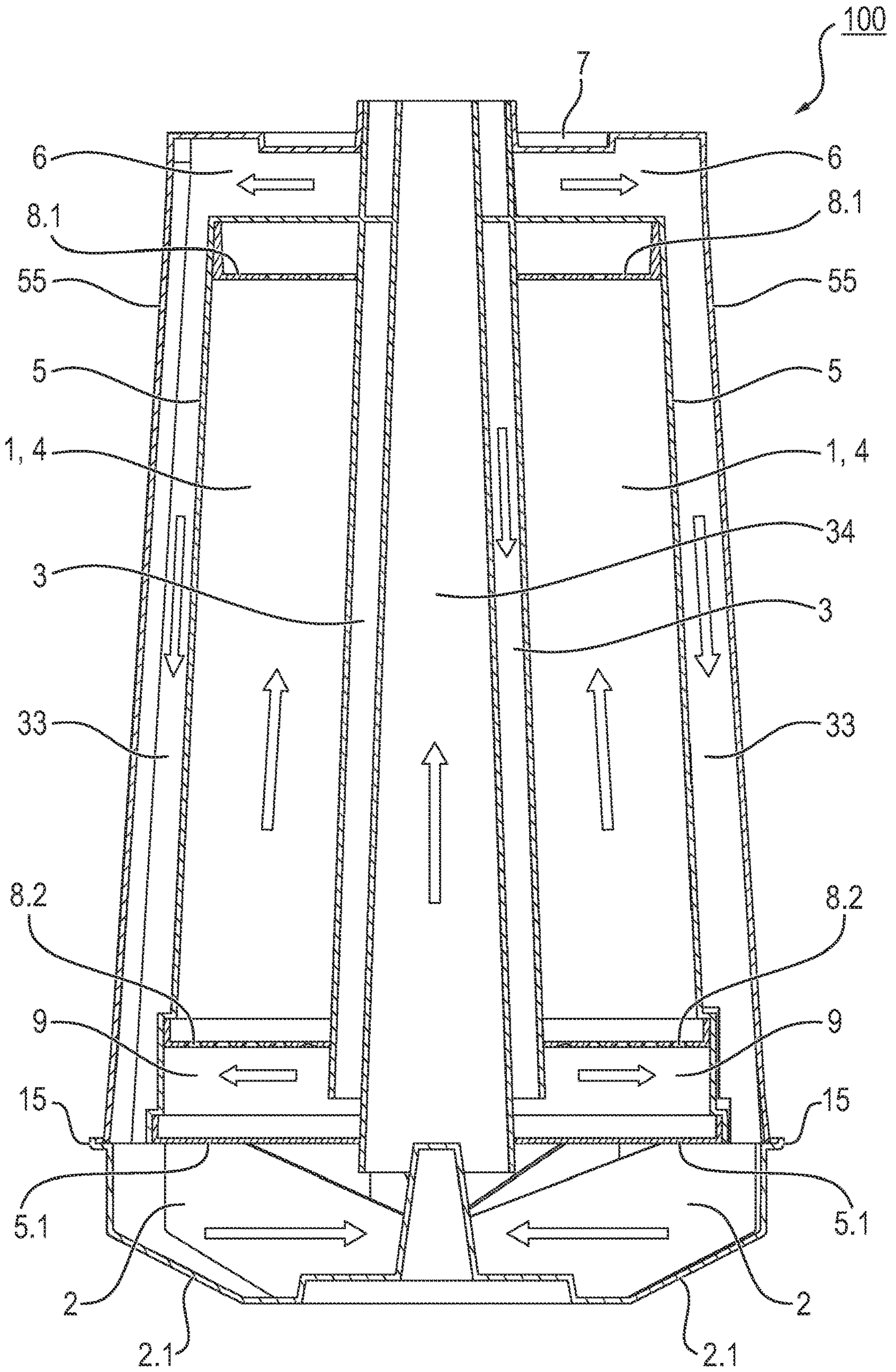
FIG. 6 is a schematic cross-sectional view showing the second embodiment.
Figure 7B:
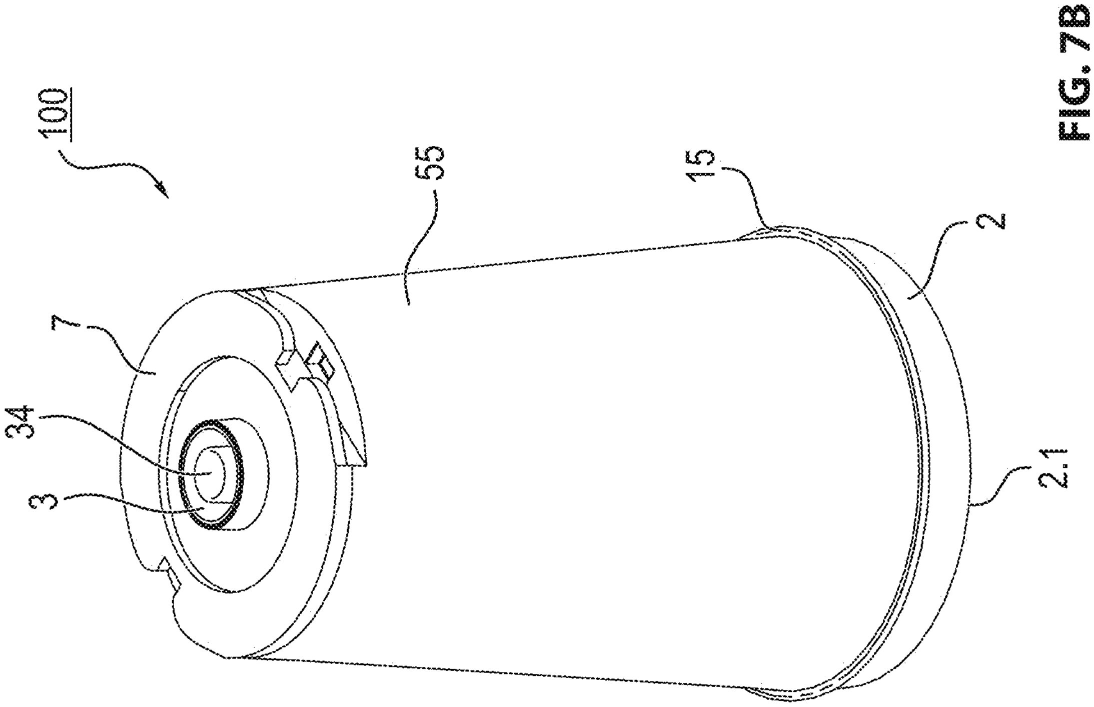
FIG. 7A is a cross-sectional perspective view and FIG. 7B is an external perspective view showing the second embodiment.
Figure 7A:
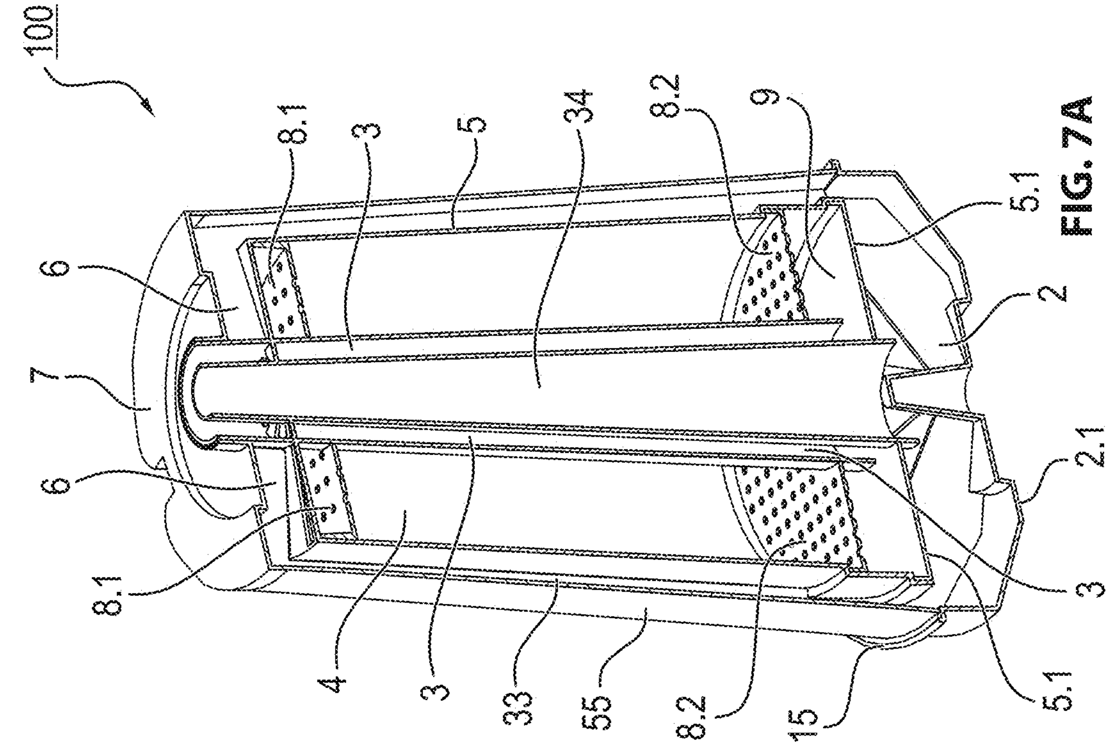

FIG. 6, FIG. 7A and FIG. 7B show a second embodiment of the absorption arrangement 100 according to the invention. In this second embodiment, the entire absorption arrangement 100 is implemented as a cartridge. This ensures a particularly compact and mechanically stable and robust implementation.

FIG. 6 shows the principle in a schematic cross-sectional view. The same parts have the same reference signs than in FIG. 3 to FIG. 5. In the second embodiment, the absorption arrangement 100 has an outer housing which accommodates and completely surrounds both the CO2 absorber 1 and the water trap 2 as well as the feed tube 3 and the connecting conduits 33, 34 and is preferably rigid. This outer housing comprises a downwardly widening upper part 55 and, as a lower part, the bottom 2.1 of the water trap 2. The water trap 2 is located below the CO2 absorber 1, and the bottom 2.1 is mechanically connected to the upper housing part 55. In one embodiment, the bottom 2.1 is releasably connected to the upper housing part 55 by a snap-in connection 15, and in another embodiment it is fixedly connected. Also, the intermediate connecting conduit 33 and the discharge connecting conduit 34 are located inside the upper housing part 55. The intermediate pieces 40.1 and 40.2 are not required in the second embodiment.

In the embodiment shown, a tubular gap occurs between the housing 5 of the CO2 absorber 1 and the upper housing part 55, which gap acts as the intermediate connecting conduit 33. Thanks to this embodiment, the intermediate connecting conduit 33 is in thermal contact with the environment over a large area, namely over at least half of the circumferential surface of the upper housing part 55. As a result, a gas mixture is cooled as it flows downwardly through the tubular intermediate connecting conduit 33.

In the realization shown, the discharge connecting conduit 34 is coaxially guided through the interior of the feed tube 3. It is also possible that the feed tube 3 is guided coaxially through the interior of the discharge connecting conduit 34.

An adapter 7 is attached to the top of the upper housing part 55. This adapter 7 can be configured in the same way as the adapter 7 of the CO2 absorber 1 of FIG. 2A and FIG. 2B. Thanks to this adapter 7, the absorption arrangement 100 can be detachably connected to the line-side coupling unit 35.

The gas mixture flows from the first section 31 through the absorption arrangement 100 according to the second embodiment to the second section 32 on the following path:

- downwards through the feed tube 3 inside the CO2 absorber 1,
- through the lower deflection cavity 9, where the gas mixture is deflected,
- upwards through the absorption material 4, where carbon dioxide is absorbed,
- upwards through the discharge cavity 6, where the gas mixture is again deflected,
- down through the intermediate connecting conduit 33, cooling the gas mixture and condensing water on the inner wall of the upper housing part 55 and in some cases on the outer wall of the housing 5,
- into the water trap 2, where the gas mixture is again diverted, and
- upwards through the discharge connecting conduit 34.

The feed tube 3 functions as the supply fluid guide unit of the second embodiment. The lower deflection cavity 9 functions as the lower deflecting fluid guide unit, and the discharge cavity 6 functions as the upper deflecting fluid guide unit. The intermediate connecting conduit 33 functions as the connecting fluid guide unit, and the discharge connecting conduit 34 functions as the discharge fluid guide unit.

FIG. 7A and FIG. 7B illustrate the second embodiment in a cross-sectional perspective view on the left and in an external perspective view on the right. The upper housing part 55 has the shape of an inverted pot. The bottom 2.1 of the water trap 2 is connected to the upper housing part 55 by a releasable or fixed connection 15. In the case of a detachable connection, the water trap 2 can therefore be detached from the upper housing part 55, emptied and reconnected.

In particular, in the second embodiment, heat is released to the environment at the following locations:

- The feed tube 3 is located between the absorption material 4 and the discharge connecting conduit 34, allowing the absorption material to transfer a high amount of heat to the feed tube 3, and allowing the feed tube 3 to transfer heat to the discharge connecting conduit 34.
- The intermediate connecting conduit 33 is located between the CO2 absorption material 4 and the upper housing part 55, allowing the intermediate connecting conduit 33 to transfer heat to the environment through the upper housing part 55.

While specific embodiments of the invention have been shown and described in detail to illustrate the application of the principles of the invention, it will be understood that the invention may be embodied otherwise without departing from such principles.

LIST OF REFERENCE CHARACTERS

| List of reference characters | |
|---|---|
| 1 | CO2 absorber, comprises the feed tube 3, the CO2 absorption material 4, the housing 5, the discharge cavity 6, the adapter 7, the two sieves 8.1 and 8.2 and the deflection cavity 9 |
| 2 | Water trap, is formed above the bottom 2.1 |
| 2.1 | Bottom of the water trap 2 |
| 3 | Centrally arranged vertical feed tube of the CO2 absorber 1, is in fluid communication with the first section 31 |
| 3.1 | Coupling-side continuation of the feed tube 3 in the coupling-side intermediate piece 40.1 |
| 3.2 | Continuation of the feed tube 3 |
| 4 | CO2 absorption material in the housing 5 |
| 5 | Housing of the CO2 absorber 1, accommodates the absorption material 4 and the cavities 6, 9, has the bottom 5.1 |
| 5.1 | Bottom of the housing 5 |
| 6 | Discharge cavity, is in fluid communication with the intermediate connecting conduit 33 |
| 6.2 | Continuation of the discharge cavity 6 in the absorber-side intermediate piece 40.2 |
| 7 | Adapter of the CO2 absorber 1, can be detachably connected to the line-side coupling unit 35 |
| 7.1 | Adapter for connecting the coupling-side intermediate piece 40.1 to the line-side coupling unit 35 |

-continued

| List of reference characters | |
|---|---|
| 7.2 | Adapter for connecting the absorber-side intermediate piece 40.2 to the coupling-side intermediate piece 40.1 |
| 8.1 | Upper sieve between the absorption material 4 and the discharge cavity |
| 8.2 | Lower sieve between the absorption material 4 and the deflection cavity 9 |
| 9 | Deflection cavity between the lower sieve 8.2 and the bottom 5.1 of the CO2 absorber 1 |
| 10 | Ventilator blower, maintains a flow of gas in the ventilation circuit. |
| 11 | Inspiratory valve, causes a regulated volume flow through the inspiratory line 30 |
| 12 | Expiratory valve, causes a regulated volume flow through the expiratory line 31, 32 |
| 13 | Lung pressure valve (PEEP saver valve) in the first section 31, ensures maintenance of an end-expiratory lung pressure |
| 14 | Coupling unit on the patient side, connected to lines 30 and 31 |
| 15 | Detachable connection between the bottom 2.1 of the water trap 2 and the housing part 55 |
| 20 | Pressure sensor, measures the pressure in the inspiratory line 30 |
| 21 | Volume flow sensor, measures the volume flow in the inspiratory line 30 |
| 22 | Pressure sensor, measures the pressure in the expiratory line 31, 32 |
| 30 | Inspiratory line, leading from the blower 10 to the patient-side coupling unit 14 |
| 31 | First section of the expiratory line, leads from the patient-side coupling unit 14 to the absorption arrangement 100 |
| 32 | Second section of the expiratory line, leading from the absorption arrangement 100 to the blower 10 |
| 33 | Intermediate connecting conduit, leads from CO2 absorber 1 to water trap 2 |
| 33.a | Corrugated hose of the intermediate connecting conduit 33 |
| 33.b | Rigid tube of the intermediate connecting conduit 33 |
| 34 | Discharge connecting conduit, guiding from the water trap 2 to the second section 32 |
| 34.1 | Continuation of the discharge connecting conduit 34 in the coupling-side intermediate piece 40.1 |
| 34.a | Corrugated hose of the discharge connecting conduit 34 |
| 34.b | Rigid tube of the discharge connecting conduit 34 |
| 35 | Line-side coupling unit between the absorption arrangement 100 on the one hand and the two sections 31 and 32 of the expiratory line on the other hand |
| 36.1 | Receptacle in the coupling-side intermediate piece 40.1 for the tube 33.b of the intermediate connecting conduit 33 |
| 36.2 | Receptacle in the coupling-side intermediate piece 40.1 for the tube 34.b of the discharge connecting conduit 34 |
| 40.1 | Coupling-side intermediate piece, is arranged between the CO2 absorber 1 and the line-side coupling unit 35 |
| 40.2 | Absorber-side intermediate piece, is arranged between the coupling-side intermediate piece 40.1 and the CO2 absorber 1 |
| 50 | Anesthetic dispenser producing a gas mixture comprising an anesthetic |
| 51 | Anesthetic supply line, opens into the inspiratory line 30 |
| 55 | Upper housing part of the outer housing of the absorption arrangement 100 according to the second embodiment, surrounds the CO2 absorber 1 and the connecting conduits 33, 34, carries the water trap 2 |
| 100 | Arrangement with absorber 1 and water trap 2 |
| L | Lungs of patient P |
| P | Patient, has lungs L, is connected to patient-side coupling unit 14 |

What is claimed is:

1. An absorption arrangement comprising:

a CO2 absorber configured to absorb carbon dioxide so as to filter out carbon dioxide from a gas mixture flowing through the CO2 absorber, the CO2 absorber comprising CO2 absorption material, a supply fluid guide unit, a lower deflecting fluid guide unit, and an upper deflecting fluid guide unit;

a water trap configured to receive moisture;

a discharge fluid guide unit configured to be connected to a sink for the gas mixture; and a connecting fluid guide unit connecting the CO2 absorber to the water trap, wherein the supply fluid guide unit is configured to be connected to a source of the gas mixture;

wherein the absorption arrangement is configured such that the gas mixture flows from the source first through the supply fluid guide unit, subsequently through the lower deflecting fluid guide unit, subsequently through the CO2 absorption material, subsequently through the upper deflecting fluid guide unit, subsequently through the connecting fluid guide unit, subsequently through the water trap, and subsequently through the discharge fluid guide unit to the sink, wherein the absorption arrangement is configured such that with the absorption arrangement in an operative state the gas mixture is deflected by the lower deflecting fluid guide unit to flow vertically or obliquely upwards through the CO2 absorption material and is deflected by the upper deflecting fluid guide unit to flow vertically or obliquely downwards through the connecting fluid guide unit to the water trap.

2. The absorption arrangement according to claim 1, wherein with the absorption arrangement in the operative state, the lower deflecting fluid guide unit is located below the CO2 absorption material and the CO2 absorption material is located below the upper deflecting fluid guide unit.

3. The absorption arrangement according to claim 1, wherein the connecting fluid guide unit is directly adjacent to an environment of the absorption arrangement.

4. The absorption arrangement according to claim 1, wherein the CO2 absorption material surrounds in the manner of a casing the supply fluid guide unit or at least a section of the supply fluid guide unit.

5. The absorption arrangement according to claim 1, wherein the connecting fluid guide unit or at least a portion of the connecting fluid guide unit surrounds the CO2 absorption material in the manner of a casing.

6. The absorption arrangement according to claim 1, further comprising an intermediate piece connectable to the source and connectable to the sink, wherein the CO2 absorber and the water trap are mechanically connected or connectable to the intermediate piece.

7. The absorption arrangement according to claim 6, wherein the connecting fluid guide unit is mechanically connected to the intermediate piece, and the water trap is mechanically connected to the connecting fluid guide unit and via the connecting fluid guide unit with the intermediate piece.

8. The absorption arrangement according to claim 6, wherein a portion of the upper deflecting fluid guide unit is located in the intermediate piece and/or a portion of the upper deflecting fluid guide unit is connected to the intermediate piece.

9. The absorption arrangement according to claim 6, further comprising a further intermediate piece connectable with the source or another source of a gas mixture and with the sink or another sink for a gas mixture, wherein the CO2 absorber and the water trap are selectively mechanically connectable to the intermediate piece or to the further intermediate piece.

10. The absorption arrangement according to claim 1, wherein the absorption arrangement further comprises an outer housing surrounding the CO2 absorber, the water trap, the discharge fluid guide unit, and the connecting fluid guide unit.

11. The absorption arrangement according to claim 10, wherein the connecting fluid guide unit is located between a segment of the outer housing and the CO2 absorber.

12. The absorption arrangement according to claim 10, wherein the outer housing comprises:

an upper housing part; and a lower housing part, which is mechanically connected to the upper housing part, wherein the absorption arrangement is configured such that with the absorption arrangement in the operative state, the upper housing part is located above the lower housing part, and wherein the upper housing part surrounds the CO2 absorber, and wherein the lower housing part forms a bottom of the water trap.

13. A ventilation system for artificial respiration of a patient, the ventilation system comprising:

a ventilator;

a patient-side coupling unit positionable in or on or at the body of the patient;

an inspiratory fluid connection;

an expiratory fluid connection, wherein the ventilator is connected to the patient-side coupling unit by the inspiratory fluid connection and by the expiratory fluid connection and the ventilator is configured to deliver a gas mixture through the inspiratory fluid connection to the patient-side coupling unit; and an absorption arrangement comprising:

a CO2 absorber configured to absorb carbon dioxide so as to filter out carbon dioxide from a gas mixture flowing through the CO2 absorber and comprising CO2 absorption material, a supply fluid guide unit, a lower deflecting fluid guide unit, and an upper deflecting fluid guide unit;

a water trap configured to receive moisture;

a discharge fluid guide unit configured to be connected to the ventilator; and a connecting fluid guide unit connecting the CO2 absorber to the water trap, wherein the supply fluid guide unit is configured to be connected to the patient-side coupling unit, wherein the ventilation system is configured such that a gas mixture flows from the patient-side coupling unit through the expiratory fluid connection to the ventilator and flows through the absorption arrangement when flowing through the expiratory fluid connection, wherein the absorption arrangement is configured such that the gas mixture flows from the patient-side coupling unit first through the supply fluid guide unit, subsequently through the lower deflecting fluid guide unit, subsequently through the CO2 absorption material, subsequently through the upper deflecting fluid guide unit, subsequently through the connecting fluid guide unit, subsequently through the water trap, and subsequently through the discharge fluid guide unit to the ventilator, wherein the absorption arrangement is configured such that in an operative state the gas mixture is deflected by the lower deflecting fluid guide unit to flow vertically or obliquely upwards through the CO2 absorption material and is deflected by the upper deflecting fluid guide unit to flow vertically or obliquely downwards through the connecting fluid guide unit to the water trap.

14. The ventilation system according to claim 13, wherein with the absorption arrangement in the operative state, the lower deflecting fluid guide unit is located below the CO2 absorption material and the CO2 absorption material is located below the upper deflecting fluid guide unit.

15. The ventilation system according to claim 13, wherein the connecting fluid guide unit is directly adjacent to an environment of the absorption arrangement.

16. The ventilation system according to claim 13, wherein the CO2 absorption material surrounds in the manner of a casing the supply fluid guide unit or at least a section of the supply fluid guide unit.

17. The ventilation system according to claim 13, wherein the connecting fluid guide unit or at least a portion of the connecting fluid guide unit surrounds the CO2 absorption material in the manner of a casing.

18. The ventilation system according to claim 13, wherein the absorption arrangement further comprises an intermediate piece connectable to the patient-side coupling unit and connectable to the ventilator, wherein the CO2 absorber and the water trap are mechanically connected or connectable to the intermediate piece.

19. A process for filtering carbon dioxide from a gas mixture using an absorption arrangement, which absorption arrangement comprises a CO2 absorber, a water trap, a discharge fluid guide unit, and a connecting fluid guide unit, wherein the connecting fluid guide unit connects the CO2 absorber to the water trap, the CO2 absorber comprising CO2 absorption material, a supply fluid guide unit, a lower deflecting fluid guide unit, and an upper deflecting fluid guide unit, the process comprising the steps of:

guiding the gas mixture from a source to the supply fluid guide unit;

guiding the gas mixture through the supply fluid guide unit to the lower deflecting fluid guide unit;

deflecting the gas mixture by the lower deflecting fluid guide unit such that the deflected gas mixture flows vertically or obliquely upwards;

guiding the gas mixture vertically or obliquely upwards through the CO2 absorption material;

deflecting the gas mixture by the upper deflecting fluid guide unit such that the deflected gas mixture flows vertically or obliquely downwards;

guiding the gas mixture vertically or obliquely downwards through the connecting fluid guide unit to the water trap;

causing the gas mixture to flow through the water trap;

guiding the gas mixture through the discharge fluid guide unit;

guiding the gas mixture from the discharge fluid guide unit to a sink; and as the gas mixture flows through the CO2 absorption material, absorbing carbon dioxide with the CO2 absorption material to filter carbon dioxide from the gas mixture.

20. The process according to claim 19, wherein the gas mixture is guided from a patient-side coupling unit positioned or positionable in or on or at the body of a patient through an expiratory fluid connection to a ventilator serving as the sink;

wherein the gas mixture is guided through the absorption arrangement when being guided through the expiratory fluid connection; and wherein the ventilator is configured to perform artificial respiration of the patient.

* * * * *